United States Patent [19]

O'Donnell, Jr.

[11] Patent Number: 6,106,514

[45] Date of Patent: Aug. 22, 2000

[54] LASER METHOD FOR SUBSURFACE CUTANEOUS TREATMENT

[76] Inventor: Francis E. O'Donnell, Jr., 709 The Hamptons La., Town & Country, Mo. 63017

[21] Appl. No.: 08/943,448

[22] Filed: Oct. 3, 1997

Related U.S. Application Data

[63] Continuation-in-part of application No. 08/804,931, Feb. 24, 1997.
[60] Provisional application No. 60/023,252, Aug. 12, 1996.

[51] Int. Cl.[7] .................................................. A61B 18/18
[52] U.S. Cl. ................................... 606/9; 606/13
[58] Field of Search .................. 606/2–4, 9, 13, 606/16–19; 607/88, 89, 91, 93, 100

[56] References Cited

U.S. PATENT DOCUMENTS

| | | |
|---|---|---|
| 5,057,104 | 10/1991 | Chess ............................................ 606/9 |
| 5,290,273 | 3/1994 | Tan ............................................... 606/9 |
| 5,507,790 | 4/1996 | Weiss ........................................ 607/100 |
| 5,618,284 | 4/1997 | Sand ............................................ 606/5 |
| 5,810,801 | 9/1998 | Anderson et al. ........................... 606/9 |
| 5,868,732 | 2/1999 | Waldman et al. ........................... 606/9 |
| 5,964,749 | 10/1999 | Eckhouse et al. ........................... 606/9 |

*Primary Examiner*—Linda C. M. Dvorak
*Assistant Examiner*—Bryan K. Yarnell
*Attorney, Agent, or Firm*—Seidel Gonda Lavorgna & Monaco, PC

[57] ABSTRACT

A laser method for delivery of pulsed infrared laser energy to a predetermined depth below the surface of the epidermis is disclosed. The method can be used to increase skin tone and reduce wrinkles. For the purposes of increasing skin tone, a novel method for quantifying the effect in vivo is disclosed. Post-treatment topical application of a pharmaceutical mixture including anti-inflammatory, anti-oxidant and neocollagen promoting agents can be used to increase new collagen synthesis stimulated by the present invention.

4 Claims, 9 Drawing Sheets

(5 of 9 Drawing Sheet(s) Filed in Color)

Trichrome stain of breast skin after treatment with the 1064 nm laser. The indentation causes a deeper thermal zone.

Laser Skin Toner Report

Patient: 8/7/97, Specimen 1

Number of Passes: 4        8.2% Tightening/Pass

| PASS | TIGHTENING | TIP | POWER SETTING | PULSE DURATION | WAVELENGTH |
|------|------------|-----|---------------|----------------|------------|
| 1    | 2.86%      | Red | 19 W          | 0.4 Seconds    | 980        |
| 2    | 8.07%      | Red | 19 W          | 0.4 Seconds    | 980        |
| 3    | 23.99%     | Red | 19 W          | 0.4 Seconds    | 980        |
| 4    | 38.89%     | Red | 19 W          | 0.4 Seconds    | 980        |

FIG. 7

Fig. 8

LASER METHOD FOR SUBSURFACE CUTANEOUS TREATMENT

CROSS REFERENCE TO RELATED APPLICATIONS

This application is a continuation-in-part of Ser. No. 08/804,931 filed Feb. 24, 1997, now allowed, and claims priority to provisional application Ser. No. 60/023,252 filed Aug. 12, 1996.

STATEMENT REGARDING FEDERALLY SPONSORED RESEARCH OR DEVELOPMENT

Not applicable.

BACKGROUND OF THE INVENTION

The present invention relates to generally to laser treatments and, more particularly to an apparatus and method of laser treatment of subsurface cutaneous tissue for the purpose of effecting a tightening of the skin and reducing wrinkles without significantly altering the epidermis.

Pulsed $CO_2$ lasers, erbium lasers, holmium lasers, and other infrared lasers are being used clinically to remove the epidermis and superficial reticular dermis for the purpose of laser resurfacing. Besides removing the superficial layers, there is often a significant contraction of the skin associated with these laser resurfacing technologies. This skin tightening is due to sufficient, but not excessive dermal collagen heating by the laser, and it is as important to patient satisfaction as the more youthful epidermis (skin surface) appearance achieved by laser resurfacing.

Unfortunately, in order to achieve this skin tightening, it has been necessary to remove the epidermis with the laser. This results in a raw skin surface that is unsightly, and that requires extensive wound care for weeks. Attempts to reduce these unwanted side effects by using lasers for resurfacing that do not produce undesired collateral thermal effect result in inadequate tightening of the skin. For example, a pulsed $CO_2$ laser of 100 microseconds or so duration (e.g., Tru-Pulse, Tissue Technologies, Inc., Albuquerque, N. Mex.) cause less postoperative erythema, swelling, and discomfort than pulsed $CO_2$ laser of one millisecond pulse duration (e.g., Nova-Pulse, Luxar, Inc., Redmond, Wash.), but they do not tighten the skin as much as the longer-pulsed $CO_2$ lasers.

Wrinkle removal by pulsed infrared lasers during resurfacing is a result of removal of the epidermis and reticular dermis at the same time. Skin tightening requires deeper thermal effects than wrinkle removal. Thus attempts to reduce postoperative erythema, pain and swelling by doing a more superficial resurfacing do not result in adequate skin tightening.

Prior art has used computer-based video technology to quantify the amount of tissue contraction in vitro associated with different ablative lasers such as $CO_2$ and erbium:YAG in order to compare their thermal effects. The in vivo use of such technology has been unnecessary and impractical because the ablative effects of the resurfacing laser would remove superficial ink marks necessary for analysis, and the end point of the treatment with ablative lasers is judged by the color appearance of the superficial dermis.

Prior art method such as those disclosed in U.S. Pat. Nos. 4,976,709 and No. 5,484,432, attempt to selectively treat subsurface collagen without damaging the surface have been primarily related to corneal treatment (laser thermal keratoplasty) for corrections of refractive errors using infrared wavelength greater than 1.8 micron. Moreover, treatment parameters identified were selected so as to avoid a cicatrix which might impair the transparency of the cornea. For example, preferred embodiments included small (<2 mm in diameter) spot size, short pulse duration (0.1 sec), a fluence up to $100J/CM^2$ and non-contact delivery means.

Contact handpieces and non-contact delivery means for laser treatment of the eye have included designs which allow for surface-sparing of the ocular tissues, but delivery of a photocoagulation to internal tissues such as the ciliary body in glaucoma management. In U.S. Pat. No. 5,514,125, for example, a contact handpiece for delivery of laser energy to the ciliary processes in glaucoma is described. It features a fiberoptic distal member separated from a focusing lens at the contact tip for the purpose of reducing scatter of the laser energy.

Controlled subsurface laser energy also can be used to remove hair, tattoos and varicose veins. A contact subsurface laser energy delivery system that can target the follicle and not damage the sebaceous glands and sweat glands and the skin between the hairs would be advantageous. Further a system for removing tattoos and treating varicose veins by the controlled subsurface application of laser energy to a predetermined depth is desirable. Since tattoo pigment and varicose veins can be found in subepidermal locations or deeper into the dermis, an apparatus that can variably focus the laser energy to a predetermined depth is desirable.

It is desirable, therefore, to use a novel device and method to increase skin tone to reduce wrinkles (and striae) without causing damage to the skin surface. Further, it would be desirable to include an especially small contact mechanism for the thin skin of the eyelids. It also would be advantageous to utilize an in vivo mechanism to quantify the amount of skin contraction in order to assure the operator that the treatment is suprathreshold.

SUMMARY OF THE INVENTION

It is an object of the present invention to effect a significant tightening (contracture) of the skin without appreciable damage to the epidermis.

Accordingly, it is an object of the present invention to increase skin tone by effecting a contracture of the skin without affecting the overlying epidermis.

It is a further object of the present invention to provide a method and apparatus reduce wrinkle formation by treating the underlying dermis without damage to the epidermis.

It is an object of the present invention to provide a method and apparatus to effect a significant tightening (contracture) of the skin without appreciable damage to the epidermis.

Accordingly, it is an object of the present invention to provide a method and apparatus to increase skin tone by effecting a contracture of the skin without affecting the overlying epidermis.

It is a further object of the present invention to reduce wrinkle formation by treating the underlying dermis without damage to the epidermis.

It is an object of the present invention to provide a laser treatment for skin tightening and wrinkle elimination which can be done without causing temporary disability to the patient.

It is a further object of the present invention to provide a method and apparatus that allow for repeated laser treatments as often as necessary to maintain skin tone and surface smoothness.

It is another object of the invention to provide a handpiece for contact delivery of infrared laser energy using treatment parameters determined to accomplish the foregoing objects of the invention.

It is an object of the present invention to provide a method and apparatus to performing skin tightening that avoids unwanted damage to hair follicles (hair loss) by photocoagulating the upper dermis and sparing the deeper dermal structures.

It is another object of the invention to provide a variable focus handpiece for contact delivery of laser energy wherein the variable depth of laser treatment is achieved by varying the distance between the focusing (diffuser) lens and the tip of the fiberoptic bundle.

It is another object of the invention to provide a variable focus handpiece for contact delivery of laser energy wherein the variable depth of laser treatment is achieved by varying the distances between the contact tip and the diffuser lens.

It is another object of the present invention to quantify in vivo the amount of skin shrinkage per pass with the present invention.

It is another object of the present invention to enhance the beneficial effects of the present invention by the topical application postoperatively of a pharmaceutical consisting of one or more of the agents selected from the group of compounds consisting of anti-inflammatory, anti-oxidant, and neo-collagen promoters.

It is another object of the invention to provide a method and apparatus for the delivery of deep subsurface laser energy to remove unwanted hair.

Still another object of the invention is to provide a method and apparatus for the subsurface delivery of laser energy to remove tattoos at various depths within the dermis.

Yet another object of the invention is to provide a method and apparatus for the subsurface delivery of laser energy to treat varicose veins at various depths within the dermis.

In accordance with the invention, briefly stated, the present invention provides a method and apparatus for photocoagulation of the dermis that spares the epidermis. For this domain of wavelengths, for example, the exact combination of parameters selected for power setting and spot size must delivery more than $100J/CM^2$ of laser energy fluence. With respect to pulse length, the pulse duration must be in excess of the thermal relaxation time of dermis (i.e., greater than 60 milliseconds) unless the laser delivers a train of short pulses ("micropulses") wherein the duty cycle selected results in an interval between pulses of less than approximately 60 milliseconds. For a given fluence, the pulse duration selected must be adequate to raise the temperature of the dermis to approximately 70° C. yet spare the epidermis.

The present invention uses a novel apparatus and method to increase skin tone and to reduce wrinkles (and striae) without causing damage to the skin surface. An especially small contact mechanism is used for the thin skin of the eyelids. Because there is no damage to the surface of the skin, the present invention utilizes an in vivo mechanism to quantify the amount of skin contraction in order to assure the operator that the treatment is suprathreshold. Moreover, the application of a topical pharmaceutical combination enhances the desired outcome.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 2b is an enlarged view of a portion of FIG. 2a.

DESCRIPTION OF THE PREFERRED EMBODIMENT

The method of the present invention comprises the application of laser energy to the skin to effect better skin tone. The method, as described in greater detail hereinafter, sufficiently photocoagulates the dermis but avoids damage to the epidermis to increase skin tone and reduce wrinkles. The method employs a novel laser handpiece designed to allow for subsurface photocoagulation of the dermis without attendant visible damage to the overlying epidermis. Furthermore, the method of the present invention avoids unwanted hair loss by controlling the depth of photocoagulation.

A typical handpiece for the method of this present invention is shown schematically in FIG. 4 and will be described in greater detail below. The contact handpiece with a hemispheric or convex transmissive tip is used to deliver approximately 10-watt to 250-watt pulses of 0.1 to 0.5 second duration of wavelengths of 800 nanometers to 1.79 microns and a spot size of 2 millimeters to 5 millimeters in diameter to yield a fluence of more than 100 $J/CM^2$.

A wavelength in the range of 800 nanometers to 1.79 microns is selected because this part of the spectrum is poorly absorbed by melanin in the epidermis and by hemoglobin in the dermal blood vessels. The laser energy is transmitted through the epidermis and effects shrinkage of the underlying dermis. Therefore, the risk of pigmentary disturbance and ecchymosis is reduced. Moreover, this part of the spectrum is only modestly absorbed by water making deeper penetration into the dermis possible than longer infrared wavelengths.

A pulse duration of 0.1 second to 0.5 second allows for photocoagulation effects in this range of the spectrum within the dermis by exceeding the thermal relaxation time of the dermis, estimated to be about 60 milliseconds (0.060 second). By avoiding excessively long pulse durations, the chance of thermal conduction to overlying epidermis is reduced. Obviously, deeper dermal photocoagulation allows for longer pulse duration at the same power setting. A power setting of 10 watts to 250 watts for pulse durations of 0.1 second to 0.5 second duration provides a sufficiently adequate fluence (greater than 100 J/CM$^2$) for spot sizes of 2 millimeters to 5 millimeters in diameter to effect a photocoagulation of the dermis. The pulse duration of 0.1 second to 0.5 second is effective for the intended purpose but does not burn the skin surface. By delivering sufficient energy to raise the dermal temperature to approximately 70° centigrade, a contracture of the dermis occurs.

It should be obvious that variations on these parameters are possible depending upon wavelength, power settings, pulse duration, and spot size selected.

The size of the contact tip is preferably 2 to 5 mm in diameter, but variations on the diameter are possible by adjusting the optics within the handpiece or by adjusting the shape and the curvature of the tip (asphericity) to appropriately focus the depth of the photocoagulation in the dermis. Moreover, variations in tip diameter necessitate the appropriate adjustment of power to achieve adequate fluence and adjustment of pulse duration to deliver enough energy to raise the temperature of the dermis without damaging the epidermis.

In another preferred embodiment, the extremely thin skin of the upper and lower eyelids is treated with a small contact tip (<1 mm in diameter) in order to more precisely effect a contracture of the thin dermis without damage to epidermis.

The contact handpiece is highly transmissive to the selected wavelength in order to avoid heating of the tip, which would damage the epidermis. The tip material must be highly transmissive for the selected wavelength. Examples of suitable materials include silicone, fiberglass, Pyrex glass, quartz, sapphire, diamond, polymethylmethacrylate, acrylic, and polycarbonate. The tip and the skin must be kept dry and clean during the treatment for the same reason. Various optical means can be used to defocus the laser energy at the tip. A convex or hemispheric contour to the contact tip further reduces the risk of focusing the laser energy too superficially. Incorporation of diffuser optics in the handpiece can reduce the risk of focusing the laser energy on the skin surface. The tip design may include a mechanism for cooling, such as air, gas, or liquid flow. The coolant may be refrigerated in order to further reduce the temperature at the point of contact with the skin.

In another preferred embodiment, monitoring the temperature of the contact tip can provide a sensing means to avoid thermal injury to the surface (epidermis). A thermocouple at the tip can be used. Alternatively, the temperature differential between coolant ingress and coolant egress from the tip can be used to detect unwanted temperature increases at the tip.

Figure 1:
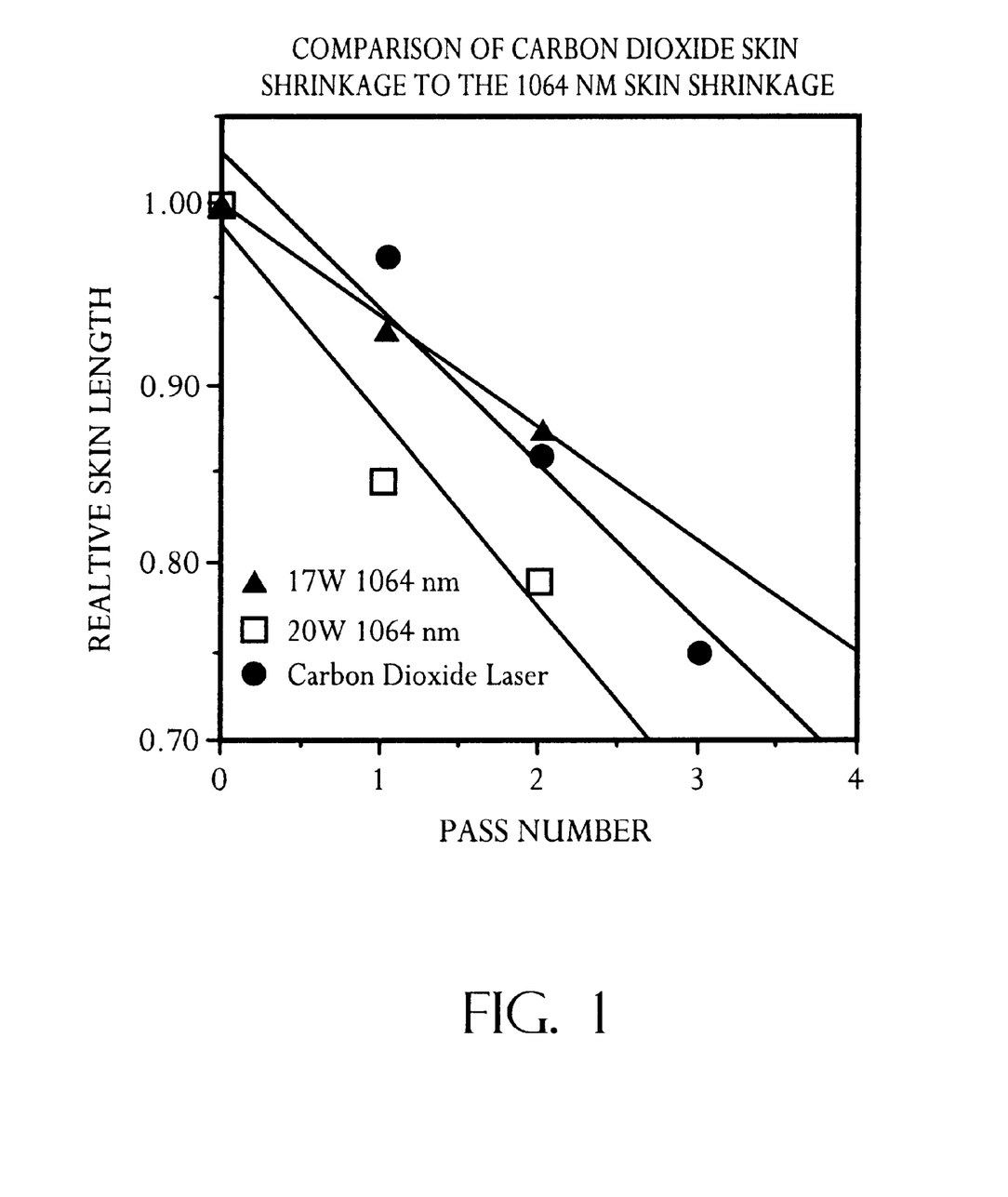
FIG. 1 is a graph illustrating the relative amount of skin shrinkage based upon the laser employed in the method of the present invention.

FIG. 1 demonstrates the linear relationship between contiguous laser spot placements (i.e., number of passes) and the amount of skin contraction using a wavelength of 1.06 microns (neodymium Nd:YAG), 0.4 second pulse duration, and a power setting of 17 watts with a hemispheric quartz tip of approximately 2.2 millimeters in diameter (fluence at the tip of approximately 180J/CM$^2$) with air cooling. For comparison, the tissue contraction induced by a pulsed $CO_2$ resurfacing laser (NovaPulse, Luxar, Inc., Redmond, Wash.) is plotted as well. The present invention is as effective as the resurfacing laser for skin contraction, but the present invention causes no damage to the skin surface (epidermis).

Figure 2A:
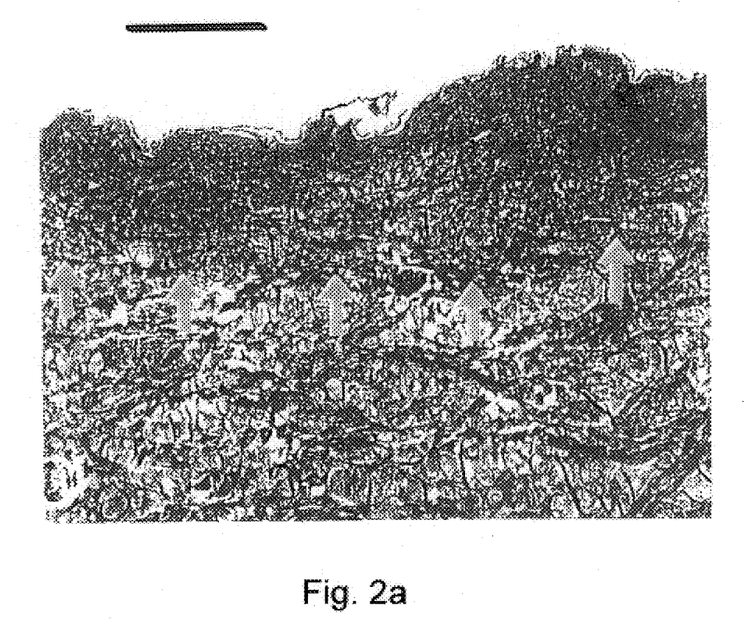
FIG. 2a is a photomicrogram illustrating breast skin treated with a 1064 nm laser.
Figure 2B:
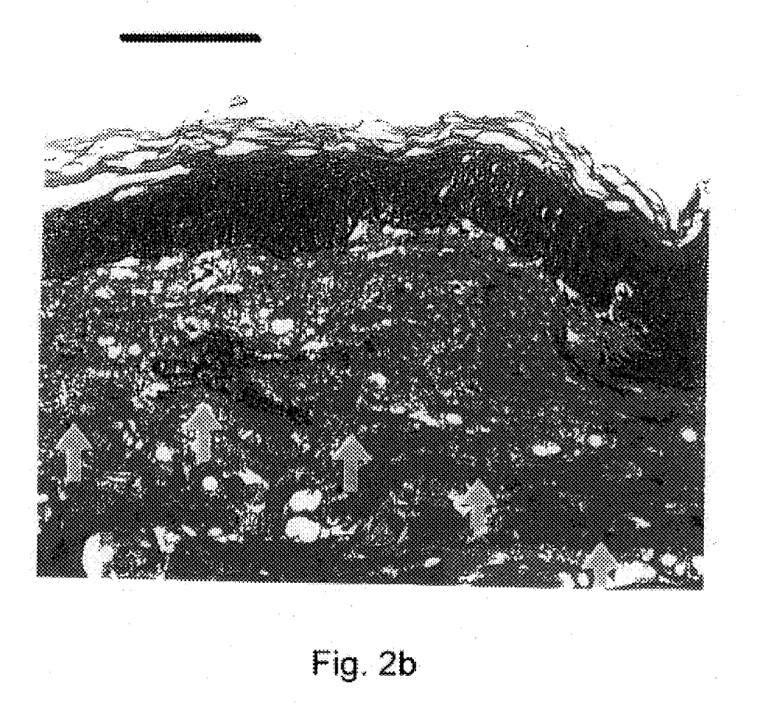

The lack of epidermal damage and the zone of photocoagulative effect in the upper dermis of the present invention is demonstrated in FIG. 2a and 2b. FIGS. 2a and 2b show a trichrime stain of breast skin after treatment with a 1064 nm laser. The black bar represents 500 microns in FIGS. 2a and 60 microns in FIG. 2b. The arrows show the approximate edges to the zones of thermal damage. It is especially noteworthy that the upper dermis (approximately 500 microns) is principally treated for the purpose of increasing skin tone and reducing wrinkles.

Figure 3:
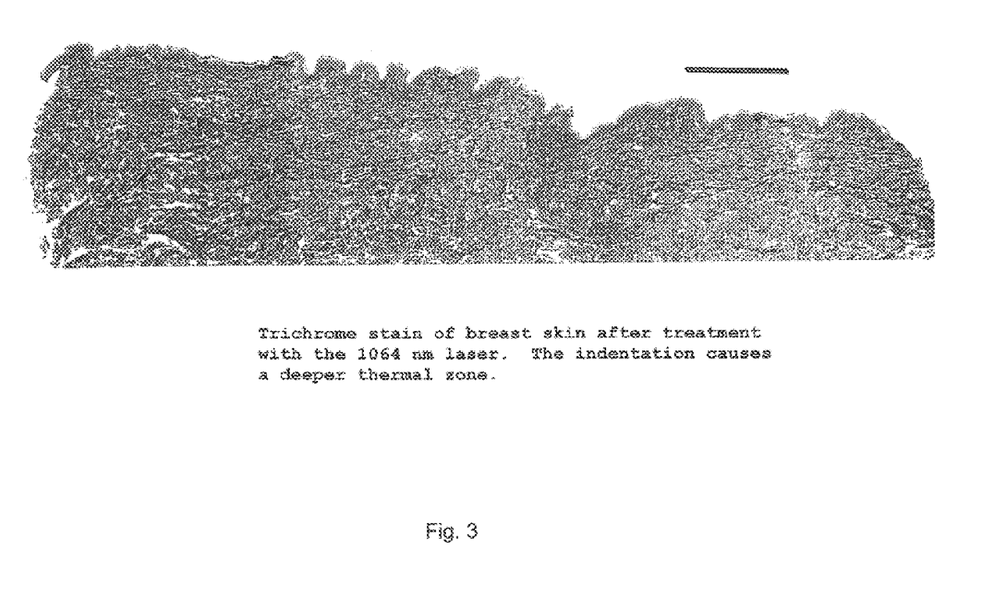
FIG. 3 is a photomicrogram illustrating breast skin treated with a 1064 nm laser.

In another preferred embodiment, firm pressure of the contact handpiece upon the skin during application of the energy deepens the depth of the photocoagulation well below the epidermal surface, a shown in FIG. 3, providing additional protection for the epidermis.

In another preferred embodiment, the placement of a diffuser lens within the handpiece between the fiberoptic element and the contact tip causes an adjustable displacement of the focal point of the laser, as will be described in greater detail below with reference to FIG. 4, so that the epidermis is spared, and the clinical effect can be modulated by depth of photocoagulation. For the purposes of increasing skin tone and reducing wrinkles, the photocoagulation effect is largely limited to the upper 500 microns of the dermis. For the purpose of destruction of hair follicles for permanent elimination of hair, the photocoagulation effect is largely limited to a band between 1.5 mm and 3.0 mm below the surface.

In another preferred embodiment of the present invention, the subsurface laser treatment is performed either before or after an ablative laser treatment (superficial laser resurfacing or a short-pulsed infrared laser treatment). Because prior art ablative lasers for resurfacing generally confine the thermal effects to the upper 100 or so microns, the present invention's ability to treat 500 or more microns of upper dermis increases significantly the desired aesthetic effect. Thus the present invention makes it possible to use superficial laser resurfacing with less superficial thermal damage and thereby allows for faster recovery and more pronounced skin tightening.

In another preferred embodiment of the present invention, the subsurface laser treatment is performed either before or after an a chemical peel. Improvements in chemical peels, such as glycolics, have made it possible to resurface the skin without a laser. Unfortunately, chemical peels do not provide sufficient tightening of the skin. The present invention is used before or after the peel to provide enhanced skin tone (skin contraction) in place of a deep laser resurfacing procedure.

Figure 8:
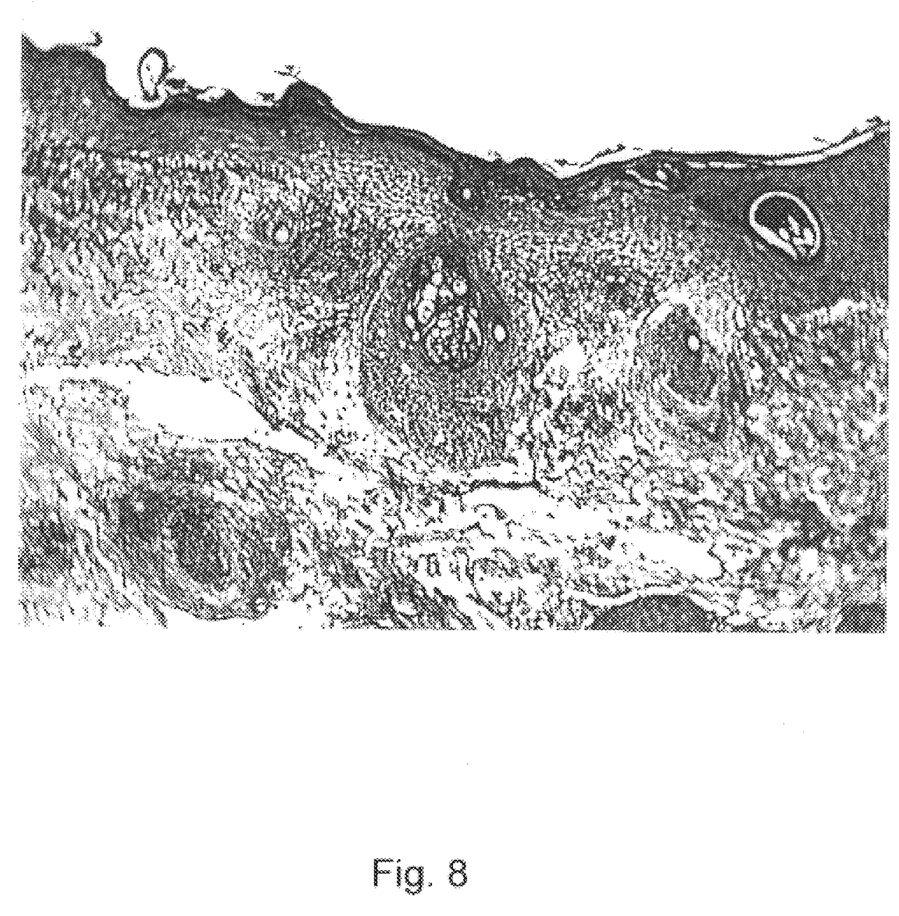
FIG. 8 is a photomicrograph of a human skin specimen harvested seven days after treatment with the present invention.

In another preferred embodiment, topical application postoperatively of a pharmaceutical mixture that promotes the desired effects on the skin is used for a period of time (approximately 30–90 days). This mixture contains one or several of the members of three classes of topical agents including anti-inflammatory, anti-oxidant, and neocollagen promoting substances. Preferred examples include respectively acetylsalicylic acid, vitamin E, and vitamin C. FIG. 8 demonstrates a photomicrograph of human eyelid skin harvested seven days after treatment with the present invention. It demonstrates significant new collagen formation in the area of treated dermis and minimal evidence of inflammation. The topical application of acetylsalicylic acid, vitamin E, and vitamin C can promote this kind of beneficial response to the laser treatment.

Figure 4:
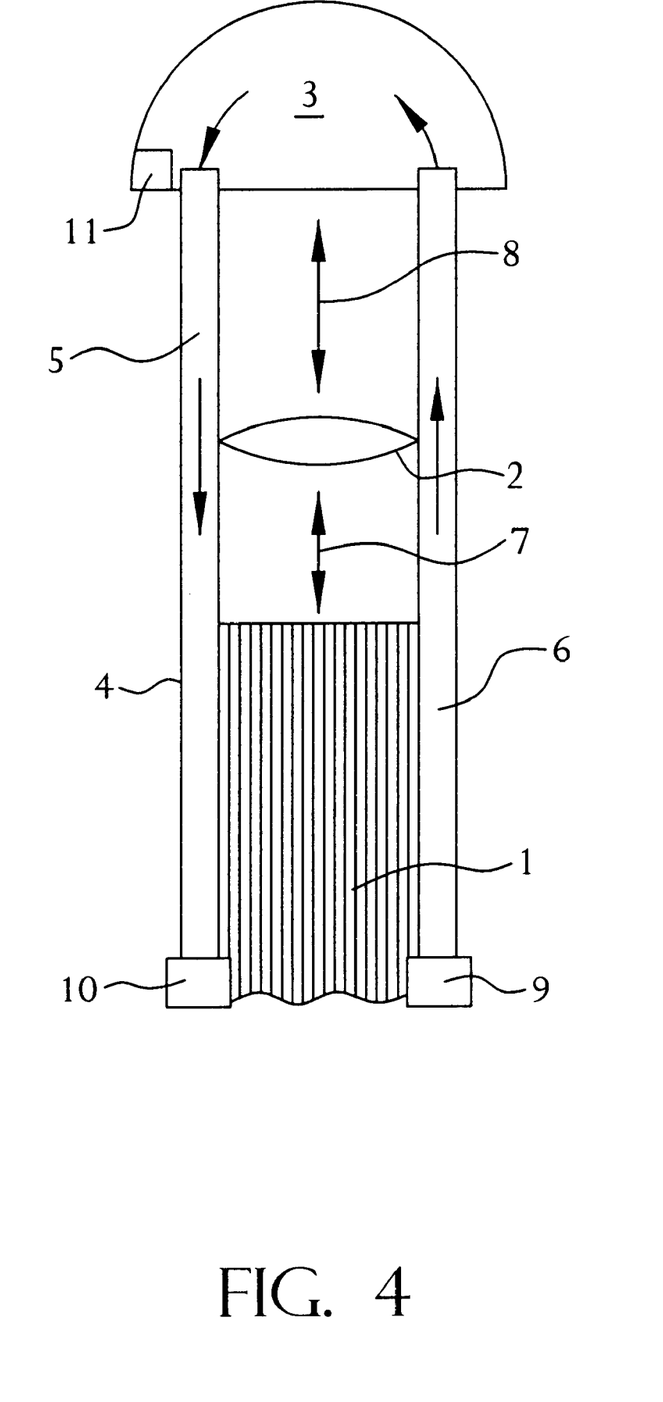
FIG. 4 is a schematic of a laser handpiece used in the method of the present invention.

FIG. 4 illustrates a preferred embodiment of the laser handpiece employed in the method. The handpiece includes a fiberoptic bundle 1, a diffuser lens 2, and a transmissive tip 3, which is the upper terminal end of a non-transmissive sleeve 4. The tip 3 which is cooled by air, gas (e.g., $CO_2$ or $N_2$) which may flow into the tip through an outer chamber 6 and return via a return path 5. Transmissive tip 3 may be constructed of materials such as fiberglass, quartz, sapphire, diamond, polymethylmethacrylate (PMMA), polycarbonate, silicone, and Pyrex glass. Transmissive tip 3 shape may be concave, plano (flat), convex (hemispheric) or annular (doughnut-shaped). Tip 3, however, is highly transmissive to avoid heat build-up at the tip. The diffuser lens 2 can be positioned during manufacturing or variably by the operator. The diffuser lens 2 can be changed in position, as shown by arrows 7 and 8, to determine the focal point of laser energy transmitted by tip 3. Diffuser lens 2 may be a convergent lens in which case the focal point is proximal to the contact tip or a divergent lens. Lens designs include biconvex, biconcave, plano-concave, plano-convex, concave and convex. The diffuser lens 2 can defocus the laser energy off the skin surface and deliver the laser energy to the dermis. Thermocouples 9 and 10 can be used to detect temperature increases at the tip 3 which could cause thermal damage to the epidermis. Alternatively, a thermocouple 11 in the tip can be used to directly sense the temperature at the tip.

Figure 5:
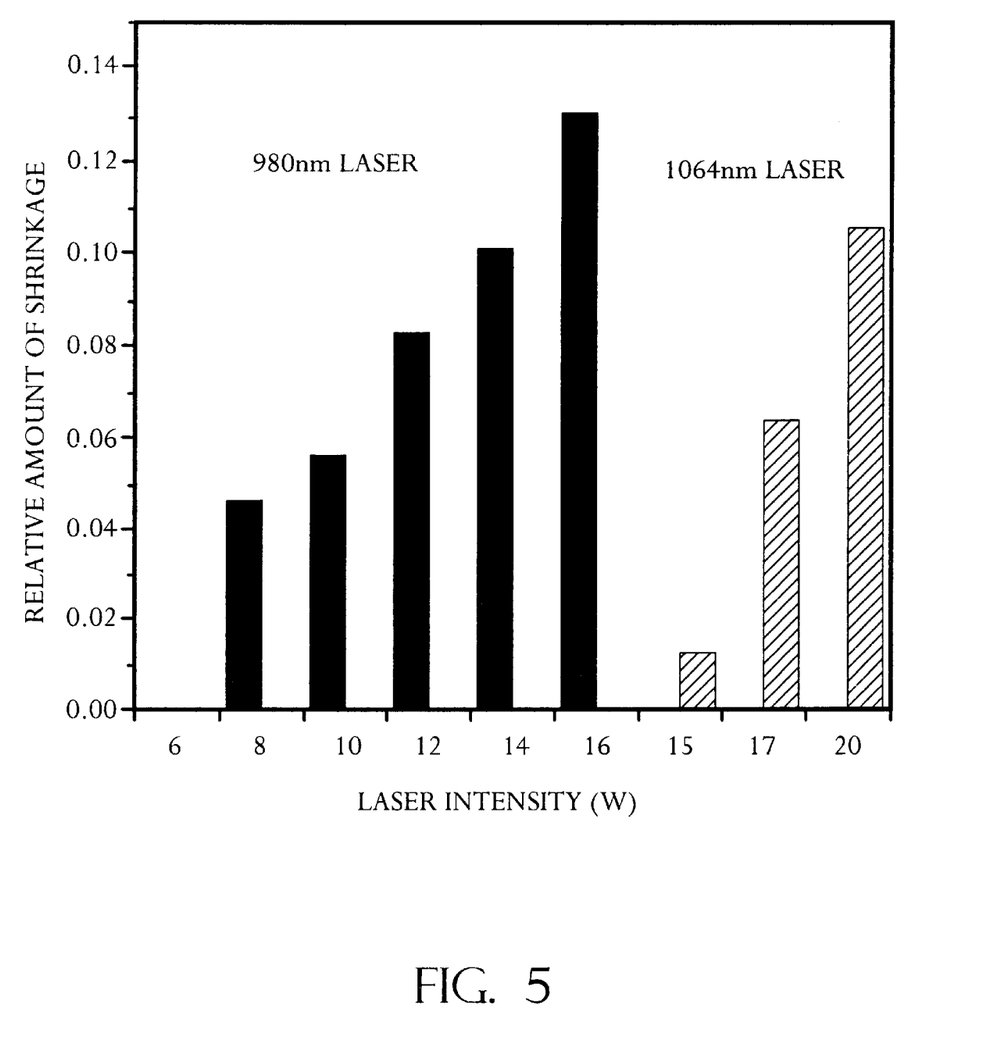
FIG. 5 is a graph illustrating the relative amount of skin shrinkage based upon the application of 1064 nm and 980 nm laser wavelengths with the present invention wherein pulse duration is held constant at 0.4 seconds.
Figure 6A:
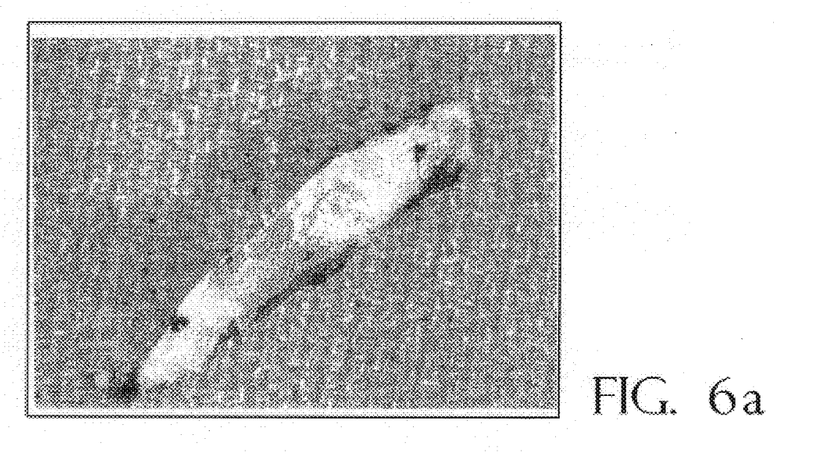
FIGS. 6a–6e are a series of specimen images with ink marks on surface at each end. Repeat images captured and digitized for analysis of relative skin shrinkage per laser pass.
Figure 6B:
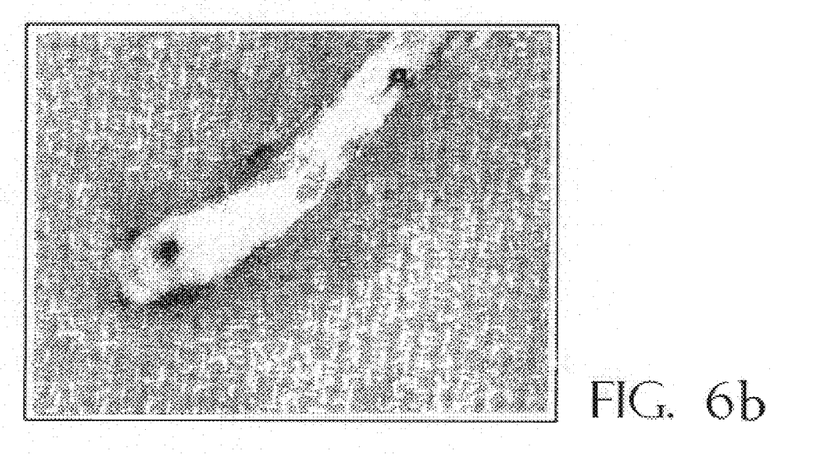
Figure 6C:
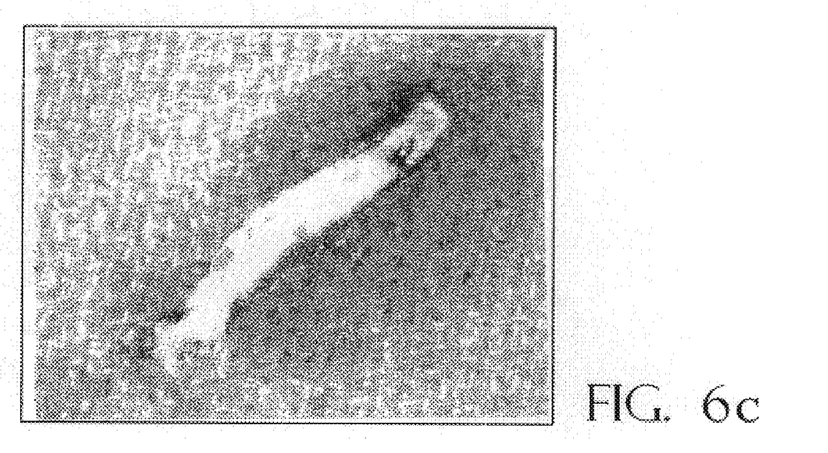
Figure 6D:
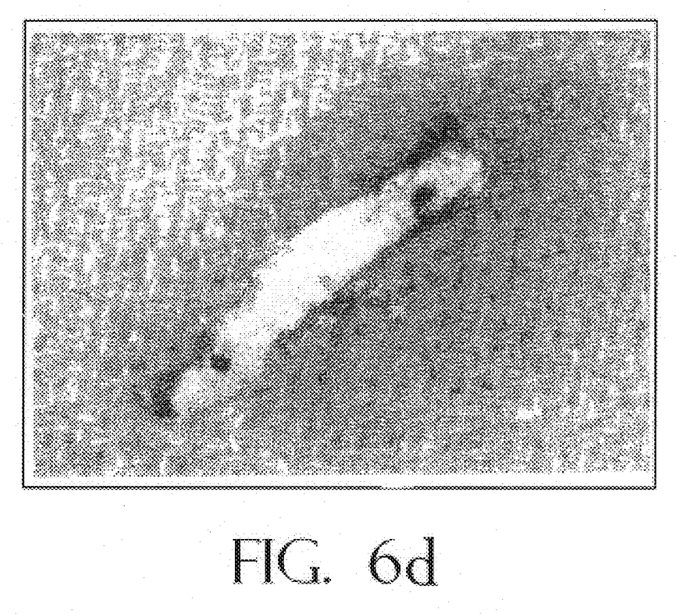
Figure 6E:
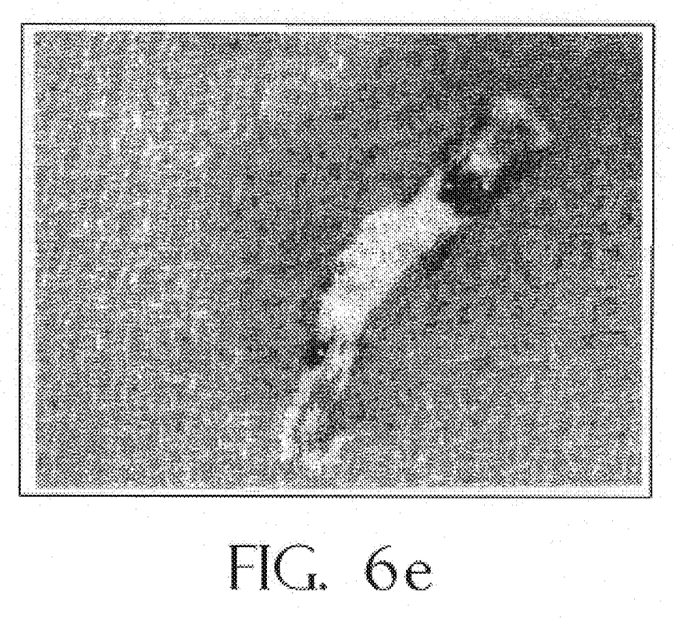

Using the device and methods of the present invention as disclosed herein, it is possible to use a large number of possible combinations of the variables of tip size, power setting, pulse duration, and wavelength to effect the controlled subsurface delivery of laser energy to a predetermined depth. FIG. 5, for example, shows the relative skin shrinkage achieved when two different wavelengths are used, and the pulse duration and contact delivery system (tip size) is held constant. Note that to achieve the same percentage contraction, the required power for 980 nm is less than for 1064 nm.

Figure 7:
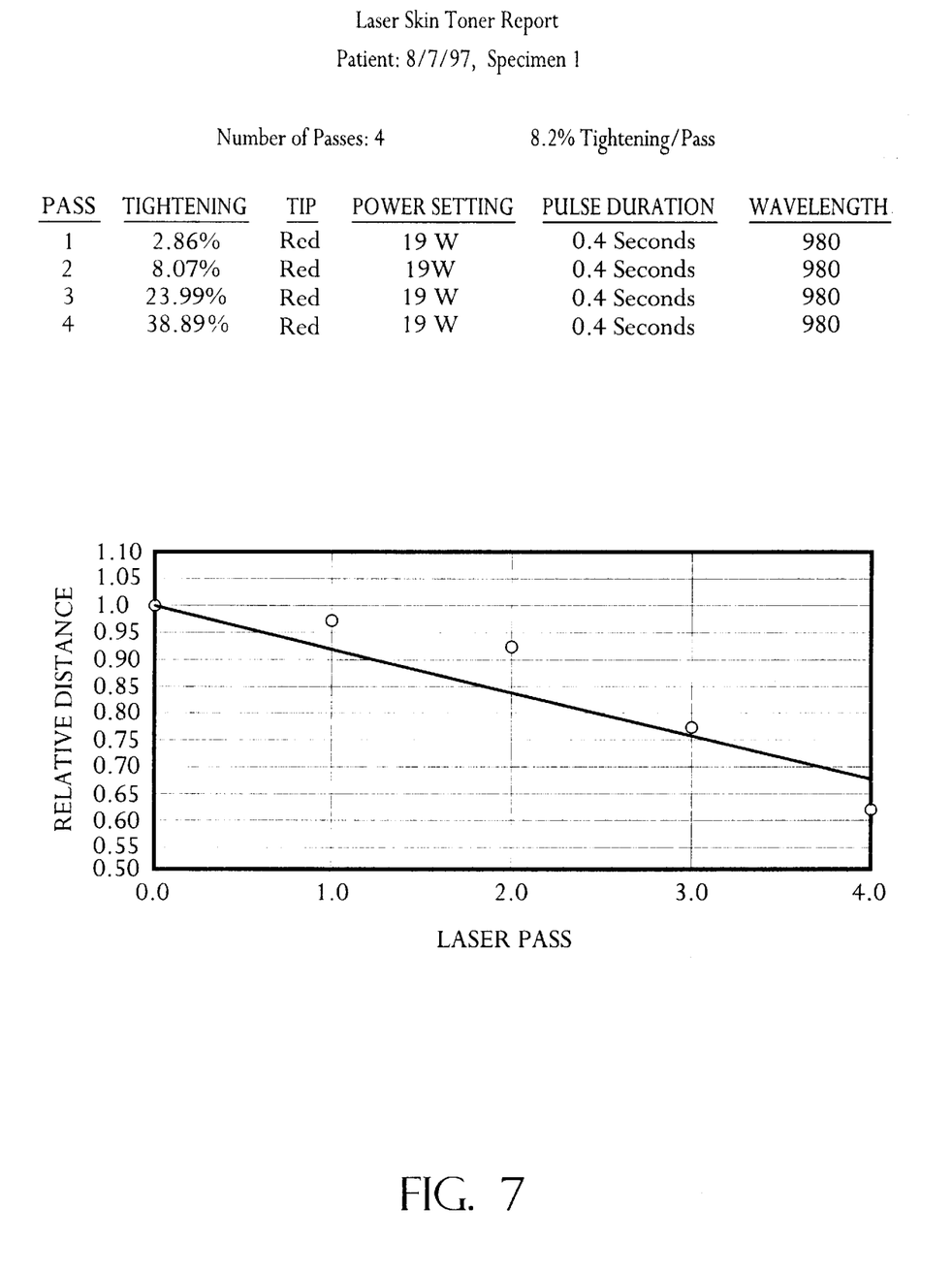
FIG. 7 is a plot of relative shrinkage with selected wavelength, pulse duration, power setting and tip of present invention.

In another preferred embodiment, the efficacy of the laser treatment to induce skin shrinkage is quantified by a PC computer-based technique wherein the magnification of images is held constant and parallax is avoided, as shown by the series of photomicrographs in FIG. 6. Ink marks are placed on the skin. An image of these marks is captured and digitized from a video of the skin to be treated. The laser parameters are selected such as power, pulse duration, diffuser lens position (including fiberoptic position and tip selection) and a pass of contiguous laser treatment is performed. A second image is captured from a repeat video. The percentage shrinkage is quantified by a simple software routine, as shown in FIG. 7. By using a CCD camera with a tight focal lens (small depth of focus), the chance of errors introduced from change of magnification is reduced. Moreover, by centering the marks in the field of view, the risk of errors introduced by parallax is reduced. This is a useful feature of the present invention, because absent unwanted visible effects on the epidermis, it can be difficult for the operator to know for sure that the treatment is suprathreshold.

To remove unwanted hair, the previously described contact handpiece is placed over the hair orifice. The handpiece can be set at an angle so as to focus the laser emission along the path of the hair to the subepidermal hair bulb. The diffuser lens 2 can be used to tightly focus the laser emission (for example, to an area less than 500 micrometers in diameter) deep in the dermis. Suprathreshold fluence at the target is achieved regardless of growth phase, pigment content or vascularization. Unlike treatment intended to increase skin tone and to reduce wrinkles which is largely confined to the top 500 microns of the dermis, treatment intended to eliminate hair is targeted at a depth 1.5 to 3.0 mm below the surface.

The method and apparatus of the present invention also can be used to remove superficial and deep tattoos from the dermis by controlled or focused application of laser energy. Moreover, a surgeon also can use the method and device to treat varicose veins of various depths. In each example, superficial lesions are treated prior to treatment of the deeper components.

It is apparent from the foregoing that various changes and modifications can be made in the method and apparatus of the present invention without departing from the scope of the appended claims. Therefore, the foregoing description and accompanying drawings are intended to be illustrative only and should not be construed in a limiting sense.

What is claimed is:

1. A method of treating a patient to increase skin tone and reduce wrinkles, comprising the steps of contacting a patient's epidermis near an area to be treated with a laser energy transmissive contact element, providing laser energy having a wavelength ranging from 800 nanometers to 1.79 microns, a power ranging from 10 to 250 watts, and a pulse duration from 0.1 seconds to 0.5 seconds from a source thereof to the epidermis through said contact element, using said contact element to focus said laser energy below the epidermis such that fluence of said laser energy in the patient's dermis below the epidermis is greater than 100 J/cm$^2$, and photocoagulating the patient's upper dermis with said laser energy while avoiding damage to the epidermis.

2. The method of claim 1 wherein the contact element comprises a handpiece.

3. The method of claim 1 further comprising the step of topically applying at least one pharmaceutical selected from the group consisting of anti-inflammatories, anti-oxidants, and neocollagen promoters to the treated area for 30 to 90 days.

4. The method of claim 3 wherein pharmaceutical comprises at least one component selected from the group consisting of acetylsalicylic acid, vitamin E, and vitamin C.

* * * * *